(12) United States Patent
Ying et al.

(10) Patent No.: US 8,766,019 B2
(45) Date of Patent: Jul. 1, 2014

(54) METHOD FOR SEPARATING BUTANOL

(75) Inventors: Hanjie Ying, Nanjing (CN); Xiaoqing Lin, Nanjing (CN); Yong Chen, Nanjing (CN); Xiaochun Chen, Nanjing (CN); Jianxin Bai, Nanjing (CN); Jian Xiong, Nanjing (CN); Wenbin Qian, Nanjing (CN); Jingjing Xie, Nanjing (CN); Jinglan Wu, Nanjing (CN)

(73) Assignee: Nanjing University of Technology, Jiangsu (CN)

( * ) Notice: Subject to any disclaimer, the term of this patent is extended or adjusted under 35 U.S.C. 154(b) by 0 days.

(21) Appl. No.: 13/814,490

(22) PCT Filed: Apr. 15, 2011

(86) PCT No.: PCT/CN2011/072890
§ 371 (c)(1),
(2), (4) Date: Feb. 26, 2013

(87) PCT Pub. No.: WO2012/016450
PCT Pub. Date: Feb. 9, 2012

(65) Prior Publication Data
US 2013/0158303 A1    Jun. 20, 2013

(30) Foreign Application Priority Data

Aug. 6, 2010 (CN) .......................... 2010 1 0250435

(51) Int. Cl.
*C07C 29/74* (2006.01)

(52) U.S. Cl.
USPC .......................................... 568/917

(58) Field of Classification Search
USPC .................................................. 568/917
See application file for complete search history.

(56) References Cited

FOREIGN PATENT DOCUMENTS

WO    WO 2008095896 A1 *   8/2008

* cited by examiner

*Primary Examiner* — Elvis O Price
(74) *Attorney, Agent, or Firm* — Christie, Parker & Hale, LLP

(57) ABSTRACT

Disclosed is a method for separating butanol. The method uses hydrophobic macroporous polymer adsorbent to separate butanol in a mixed solution, and the process comprises the following steps: 1) using macroporous polymer adsorbent to adsorb butanol in a mixed solution; 2) desorbing butanol from macroporous polymer adsorbent. The method is simple; the separation time is short; the efficiency of butanol recovery is high; and the separating cost is low.

21 Claims, 3 Drawing Sheets

METHOD FOR SEPARATING BUTANOL

CROSS-REFERENCE TO RELATED APPLICATION(S)

This application is a National Phase Patent Application and claims priority to and benefit of International Application Number PCT/CN2011/072890, filed on Apr. 15, 2011, which claims priority to and benefit of Chinese Patent Application Number 201010250435.3, filed on Aug. 6, 2010, the entire disclosure of which are incorporated herein by reference.

TECHNICAL FIELD

The present invention belongs to the technical field of biochemical separation, and relates to a method for separating butanol.

BACKGROUND ART

Biobutanol is mainly used in producing plasticizers, such as dibutyl phthalate and aliphatic dicarboxylic acid butyl esters, and is therefore widely used in the production of a variety of plastic and rubber products. Butanol can also be used to produce butyraldehyde, butyric acid, butylamine and butyl acetate, which can be used as the solvents of the resins, paints and adhesives, and also can be used as extractants of greases, drugs, and perfumes, and as additives for alkyd resin coatings. Meanwhile, butanol is also a new biofuel of great potential.

Biobutanol is produced through the method of microbial fermentation, in the method, renewable biomasses, such as starchiness, pulp waste, molasses and wild plants are used as the raw material, and *Clostridium acetobutylicum* or *Clostridium beijerinckii* is inoculated thereinto, and then acetone, butanol and ethanol and other products are produced through complicated biochemical changes. Therefore, the above fermentation process for producing biobutanol is also called ABE (acetone-butanol-ethanol) fermentation. Due to toxic effects of butanol on the bacteria, severe product inhibition occurs during the entire fermentation process, and when the concentration of butanol reaches a certain value, the microorganism stops growing, therefore, the concentration of butanol in the fermentation broth is very low, and the cost of recovering butanol by the conventional distillation method is extremely high.

In order to solve this key problem, it is necessary to adopt an effective method to remove the products of ABE from the fermentation broth, reduce the inhibition effect of the products, thereby improving the yield of fermentation and reducing the industrial cost.

Currently, major technologies for separating the fermentation products of ABE include gas stripping (GS), liquid-liquid extraction, pervaporation (PV) and adsorption. Meagher et al. (U.S. Pat. No. 5,755,967) adopt the method of pervaporation to separate acetone and butanol by developing a zeolite membrane filled with silicone rubber, and the zeolite membrane has excellent selective adsorption on acetone and butanol compared with adsorption on the ethanol, acetic acid and butyric acid. Qureshi, N. et al. (Qureshi, N., et al., 2005, Bioprocess and Biosystems Engineering, 27(4): 215-222) recover biobutanol by the method of adsorption-desorption, in terms of energy consumption, the method of adsorption-desorption is the best recovery process, which mainly studies the adsorption performances of some adsorption media, including activated carbon, bone char, siliceous rock, polymer resin XAD-4 and XAD-7, and polyvinyl pyridine resin. However, the total recovery rate of butanol is low due to the following two reasons: on the one hand, the adsorption capacity of the adsorption media is low, such as less than 100 mg butanol/g adsorbent; on the other hand, butanol cannot be desorbed from the adsorbent effectively. DIJK et al. (WO 2008/095896 A1) separate biobutanol by using a hyper-crosslinked microporous resin, but the resin adsorbs a certain amount of acetone and ethanol, which increases the cost for later separation processes. Arjan Oudshoorn et al. (Biochemical Engineering Journal 2009, 48:99-103) adopt the zeolite to adsorb and separate biobutanol, and investigate adsorption performances of three zeolites including CBV28014, CBV811, CBV901 on biobutanol, but the problems of this method are that the adsorption capacity of the zeolite on the biobutanol is not high, and acetone and ethanol are also adsorbed while butanol is adsorbed, resulting in the increase of cost for later separation. David R. Nielsen et al. (Biotechnology and Bioengineering 2009, 102(3): 811-821) recover biobutanol in situ by utilizing a polymer resin, and investigates the adsorption performance of the polymer resin on biobutanol, but there are problems on this method, for example the resin contacts with the fermentation broth directly, causing contamination to the resin, some resins have poor biocompatibility, and can adsorb the substrate of glucose and intermediates of the fermentation reaction, some resins have relatively low adsorption capacity, and the resins adsorb large amounts of acetone and ethanol although they have higher adsorption capacity on butanol.

SUMMARY OF THE INVENTION

The object of the present invention is to provide a novel method for separating butanol, to recover butanol economically and effectively.

The above object of the present invention is implemented by the following technical solution.

The present invention provides a method for separating butanol, which includes the following steps: 1) adsorbing butanol in a mixed solution by a hydrophobic macroporous polymer adsorbent to reach saturation; 2) desorbing butanol from the hydrophobic macroporous polymer adsorbent through a method of thermal desorption.

Preferably, the adsorption temperature in the step 1) is 30~37° C.

Preferably, the step 1) further includes the step of shaking the mixed solution at a rate of 20~250 rpm during adsorption.

Preferably, the weight volume ratio (g/mL) of the hydrophobic macroporous polymer adsorbent to the mixed solution used in the step 1) is 1:50.

Preferably, the desorption temperature in the step 2) is above 120° C.

Preferably, the initial concentration of the butanol in the mixed solution is 5~350 g/L.

Preferably, the mixed solution further includes ethanol and acetone, preferably from fermentation broth;

Preferably, the butanol is n-butanol.

Preferably, the method further includes the step of regenerating the hydrophobic macroporous polymer adsorbent; more preferably, the regeneration of the hydrophobic macroporous polymer adsorbent and desorption of the butanol are completed simultaneously.

Preferably, the step 1) further includes the step of shaking the mixed solution at a rate of 20~250 rpm during adsorption.

Preferably, the hydrophobic macroporous polymer adsorbent is selected from one or more of the group consisting of styrene-diethyl benzene, polyacrylamide, amide group cyano group and phenolic hydroxyl.

Preferably, the inner surface area of the hydrophobic macroporous polymer adsorbent is 100~2000 m²/g.

Preferably, the particle size of the hydrophobic macroporous polymer adsorbent is 20~60 mesh.

Preferably, the pore diameter of the hydrophobic macroporous polymer adsorbent is 1~180 nm; and the pore volume of the hydrophobic macroporous polymer adsorbent is 0.4~3 cm³/g.

Preferably, the wet apparent density of the hydrophobic macroporous polymer adsorbent is 590~750 g/L;

Preferably, the water content of the hydrophobic macroporous polymer adsorbent is 40~80%.

In a preferred embodiment of the present invention, the following two hydrophobic macroporous polymer adsorbents are selected to separate butanol: one adsorbent is a non-polar resin, which has a skeleton structure of styrene-diethyl benzene without any functional group, and mainly relies on the n-alkyl side chain of butanol and the benzene ring in the skeleton structure of styrene-diethyl benzene to generate hydrophobic interaction force, that's to say, a hydrophobic interaction force; and another adsorbent is a polar resin, which has a skeleton structure of polyacrylamide, and its functional groups are generally polar functional groups containing nitrogen, oxygen or sulfur, such as amide group cyano group and phenolic hydroxy, and the adsorbent mainly relies on the alcoholic hydroxyls of butanol and hydroxyls of polar functional groups in the polar adsorbent resin to generate hydrogen bonding force. After the hydrophobic macroporous polymer adsorbent adsorbs the solution containing acetone, butanol and ethanol to reach saturation, water is used to wash the residual solution which is not adsorbed first, and then butanol is desorbed from the adsorbent through the method of thermal desorption while the adsorbent is regenerated.

Butanol is a hydrophobic and volatile substance, and mainly relies on the adsorption force caused by van der Waals forces and hydrogen bonds to combine with the adsorbent, the present invention finds that the adsorption force between the adsorbent and butanol can be destroyed by heating butanol, for example, heating up to near boiling point, therefore it is easier to desorb and recover butanol with the method of thermal desorption, and there are significant differences on desorption and recovery of butanol at different thermal desorption temperatures. Moreover, the skeletal structures and functional groups of the different adsorbents are different, resulting in different hydrophobic interaction forces between the resins and butanol, which will affect the adsorption and desorption of the resins. The desorption rate of the used hydrophobic macroporous polymer adsorbents through screening in the present invention can reach above 95%, while the highest desorption rate of the resins reported can only reach 85%.

In summary, the present invention is mainly advantaged in that: using the method of thermal desorption, butanol can be desorbed from the adsorbent more effectively while the adsorbent also can be regenerated, and based on the difference between the affinity of the macroporous polymer adsorbent with the target substance of butanol and that with the impurities such as acetone and ethanol, efficient separation of butanol from acetone and ethanol is further achieved by using the hydrophobic macroporous polymer adsorbent which only adsorbs butanol but does not adsorb or adsorbs smaller amount of functional groups of acetone and ethanol. Thus, it can be seen that, the method of the present invention has advantages of novel conception, simple process, short separation time, high recovery efficiency of butanol, low cost of production, and has good prospect of promotion. Experiments show that, using the method of the present invention, nearly 70% of butanol can be adsorbed within 30 min, and absorption of butanol can reach 95% after 9 hours, wherein purity of butanol can reach above 99%.

BRIEF DESCRIPTION OF THE DRAWINGS

Hereinafter, the embodiments of the present invention will be illustrated in detail in combination with the accompanying drawings, wherein.

DETAILED DESCRIPTION OF PREFERRED EMBODIMENTS

The present invention will be illustrated with reference to specific examples hereinafter. Those persons skilled in the art will appreciate that these examples are merely used to illustrate the present invention, rather than limit the scope of the present invention in any way.

In each of the following examples, the concentration of the mixed solution of acetone, butanol and ethanol (ABE) is detected through the high performance liquid chromatography, the used instruments and conditions for detection are as follows: Agilent 1200 high performance liquid chromatograph (DAD diode array detector), and Aminex HPX-87H chromatographic column (φ300×7.5 mm) are used, the mobile phase is 0.5 mmol/L sulfuric acid solution, with a flow rate of 0.500 mL/min, the column temperature is 15° C., the injection volume of sample is 20 μL, and a differential refractive index detector is used for detection.

In each of the following examples, the adsorption capacity of the macroporous polymer adsorbent is calculated by the following formula:

$$q_e = \frac{(C_0 - C_e)V}{W}$$

wherein $C_0$ represents the initial solubility (g/L) of butanol; $C_e$ represents the equilibrium solubility (g/L) of butanol; V represents the volume (L) of a butanol solution; and W represents the mass (g) of a macroporous polymer adsorbent.

Example 1

In this example, the adsorption capacities of different hydrophobic macroporous polymer adsorbents on acetone, butanol and ethanol in the mixed solution are measured, which is described specifically as follows.

An ABE solution of a certain concentration was prepared, and 1 g different dry macroporous polymer adsorbents ($L_{1-19}$ are respectively resins of Amberlite series, Diaion series and D series) after air pump filtration were respectively added into the ABE solution, after the adsorbent reaches adsorption saturation, the adsorption capacity of the macroporous polymer adsorbent on the ABE and the separation factor were calculated through the high performance liquid chromatography method (HPLC).

Figure 1:
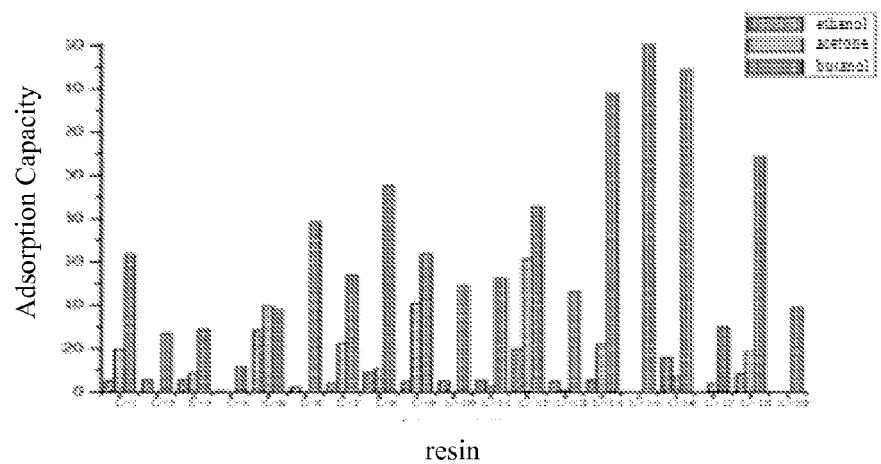
FIG. 1 shows results of adsorption capacities of various macroporous polymer adsorbents measured in Example 1 of the present invention.

The experimental results are shown in FIG. 1. It can be seen from FIG. 1 that the adsorption capacities of resins of Diaion series (L-2, L-3, L-4, L-13, L-17) on butanol are relatively low, and the L-17 resin also adsorbs a small amount of byproducts such as acetone while adsorbing butanol; resins of D-series (L-1, L-5, L-6, L-7, L-8, L-9, L-10, L-11, L-12, L-14, L-16, L-18) have slightly higher adsorption capacities on butanol, but these resins also adsorb byproducts such as acetone and ethanol at the same time; resins of Amberlite series (L-15, L-19) have extremely high adsorption capacities on butanol, and does not adsorb byproducts such as acetone and ethanol.

Methods for measuring various parameters of resins are as follows: the water content of the resins is measured according to the method described in the literature (GB5757-86[S]); the content of active groups of the resins and the apparent density ($r_a$) of the resins are measured with reference to the method disclosed in the literature (Binglin He, Wenqiang Huang, Ion exchange and adsorption resins [M]. Shanghai: Shanghai Science and Technology Education Press, 1995); special surface area of the resins is measured with reference to the literature (Qiming Tan, Zuoqing Shi. Measuring specific surface of resins with simple nitrogen adsorption method [J]. Ion Exchange and Adsorption, 1987, 3(1): 30) by using a simple BET instrument; pore volume is calculated according to the formula $V_{pore\ volume}=1/r_a-1/r_T$; and the average pore diameter is calculated according to the formula $r=2\ V_{pore\ volume}/S$.

Example 2

Figure 2:
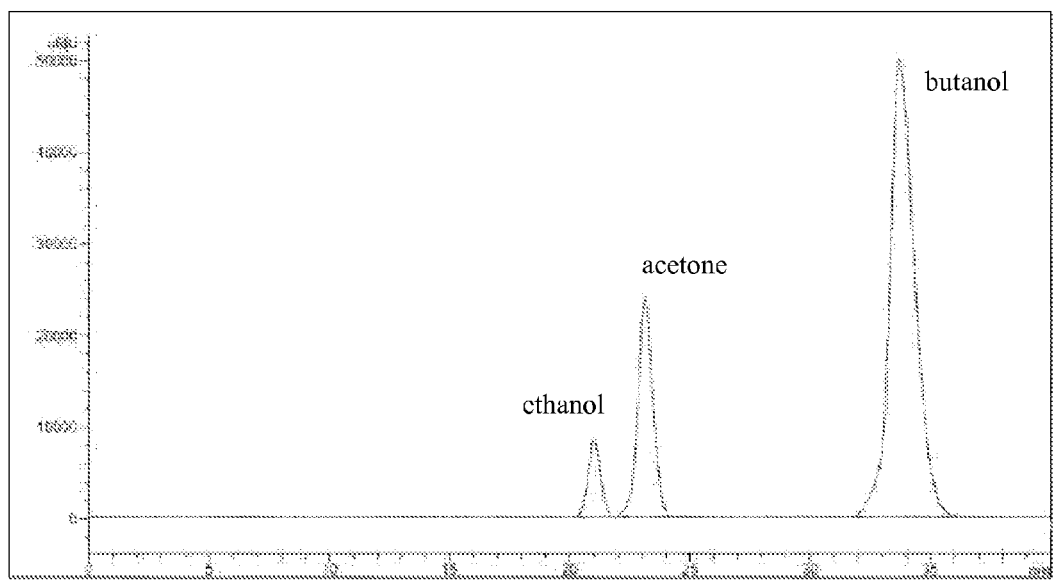
FIG. 2 is a chromatogram of a mixed solution of acetone, butanol and ethanol (ABE) measured in Example 2 of the present invention.

In this example, butanol is separated from the mixed solution using the L15 macroporous polymer adsorbent of Example 1, which specifically includes the following steps:
1) 50 mL mixed solution containing acetone, butanol and ethanol (ABE) (its chromatogram is shown in FIG. 2) was placed in the 37° C. thermostatic water bath with stirring speed of 200 rpm, and 1 g macroporous polymer adsorbent was used to adsorb the mixed solution to reach saturation (over 24 hours);
2) the water in at least doubled amount of resin (V/V) was used to wash the residual solution which was not adsorbed;
3) the adsorbent was heated to 120° C., and butanol was desorbed from the adsorbent while the regenerated adsorbent was obtained.

Example 3

In this example, adsorption kinetics of butanol was studied by using the L15 macroporous polymer adsorbent of Example 1.

Figure 3:
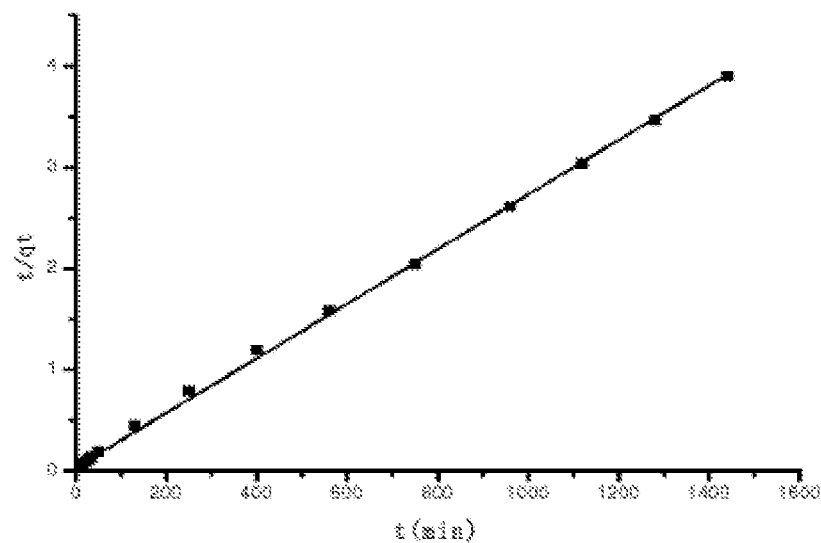
FIG. 3 is an adsorption kinetic pseudo second-order equation fitting diagram of a macroporous polymer adsorbent measured in Example 3 of the present invention.

1 L butanol solution of 16.196 g/L was prepared, and 20 g wet macroporous polymer adsorbent was added thereinto, and placed in 37° C. thermostatic water bath with stirring speed of 200 rpm, the solution was sampled at different times, and the concentration of butanol was detected through the high performance liquid chromatography method, the specific results are shown in Table 1, wherein adsorption rate of butanol is calculated through dividing the adsorption capacity at each time point by the adsorption capacity at 1,440 min. The data were fitted with a pseudo second-order equation, and the results are shown in FIG. 3.

TABLE 1

Concentration analysis results of butanol in the solution phase at different times

| Nos. | Time (min) | Concentration of butanol (g/L) | Adsorption rate of butanol (%) |
|---|---|---|---|
| 1 | 0 | 16.196 | 0 |
| 2 | 0.5 | 15.200 | 13.5% |
| 3 | 1.0 | 14.511 | 22.8% |
| 4 | 1.5 | 14.211 | 26.9% |
| 5 | 2.0 | 13.476 | 36.8% |
| 6 | 3.0 | 13.156 | 41.1% |
| 7 | 4.0 | 12.968 | 43.7% |
| 8 | 5.0 | 12.623 | 48.4% |
| 9 | 7.0 | 12.336 | 52.2% |
| 10 | 9.0 | 12.291 | 52.8% |
| 11 | 12.0 | 11.885 | 58.3% |
| 12 | 15.0 | 11.860 | 58.7% |
| 13 | 18.0 | 11.841 | 58.9% |
| 14 | 21.0 | 11.326 | 65.9% |
| 15 | 25.0 | 11.312 | 66.1% |
| 16 | 30.0 | 11.222 | 67.3% |
| 17 | 35.0 | 11.176 | 67.9% |
| 18 | 50.0 | 11.057 | 69.5% |
| 19 | 130.0 | 10.453 | 77.7% |
| 20 | 250.0 | 9.881 | 85.5% |
| 21 | 400.0 | 9.512 | 90.5% |
| 22 | 560.0 | 9.140 | 95.5% |
| 23 | 750.0 | 8.862 | 99.3% |
| 24 | 960.0 | 8.845 | 99.5% |
| 25 | 1120.0 | 8.828 | 99.7% |
| 26 | 1280.0 | 8.808 | 99.9% |
| 27 | 1440.0 | 8.807 | 100% |

Example 4

In this example, butanol adsorption isotherms at different temperatures are tested, the specific process is as follows.

50 mL ABE solutions of different concentrations were prepared, 1 g wet L15 macroporous polymer adsorbent was added thereinto, and respectively placed in shaking tables of 10° C., 20° C., 30° C. and 37° C. with stirring speed of the shaking table being 200 rpm, and the equilibrium concentration of the solution was detected when the macroporous polymer adsorbent adsorbed the mixed solution to reach saturation.

Figure 4:
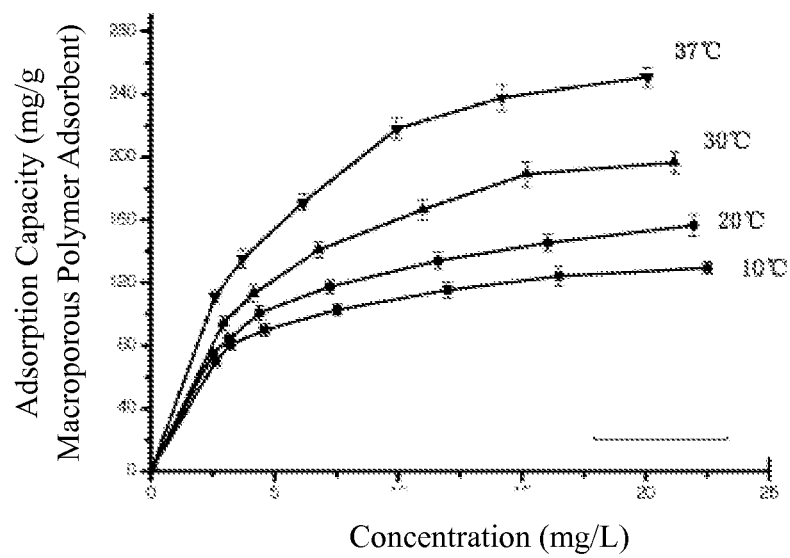
FIG. 4 shows adsorption isotherms of a macroporous polymer adsorbent at different temperatures measured in Example 4 of the present invention.

The adsorption isotherms were drawn, as shown in FIG. 4. It can be seen from FIG. 4 that, the adsorption capacity of butanol increases as temperature rises, and the adsorption capacity reaches the maximum at 37° C.

Effects of butanol solutions of different initial concentrations on the L-15 macroporous polymer adsorbent are tested in the following.

13 bottles of 50 mL ABE solutions of different concentrations were prepared, 1 g wet macroporous polymer adsorbent was added thereinto respectively, and placed in 37° C. shaking table with stirring speed of the shaking table being 200 rpm, and the equilibrium concentration of the solution was detected when the macroporous polymer adsorbent adsorbed the solution to reach saturation.

Figure 5:
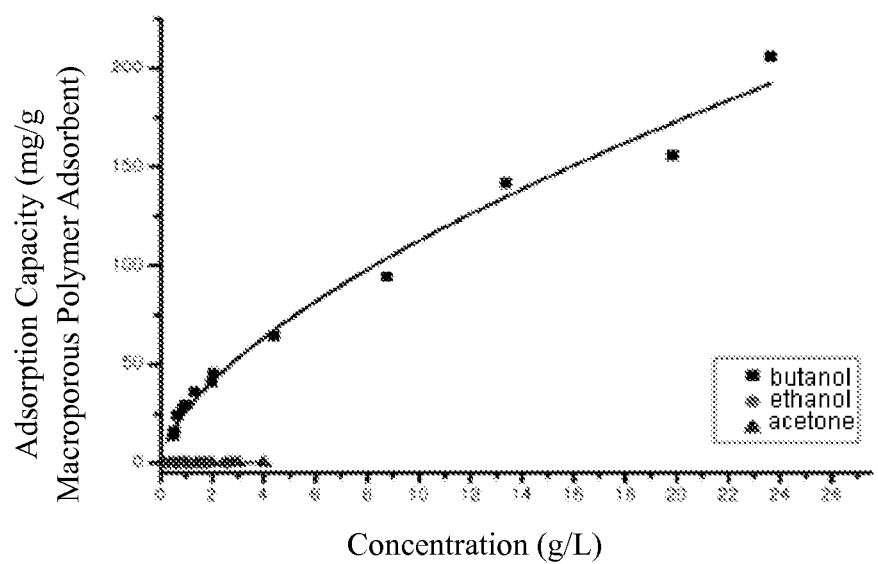
FIG. 5 shows effects of different initial concentrations of butanol on a macroporous polymer adsorbent which are measured in Example 4 of the present invention.

FIG. 5 shows a curve representing the relation between the concentrations of butanol in two phases when butanol molecules reach equilibrium during process of adsorption at the interface of two phases at a certain temperature (37° C.). It can be seen from FIG. 5 that the adsorption of the macroporous polymer adsorbent on butanol is accorded with the Langmuir adsorption model. It can be known from the calculation of adsorption isotherms at different temperatures that, the adsorption of the resin on butanol is a favorable process.

Specifically, experimental data were fitted through the Langmuir adsorption isotherm model linear formula:

$$\frac{C_e}{q_e} = \frac{1}{q_o K_L} + \frac{1}{q_o} C_e$$

by measuring adsorption isotherms at different temperatures, so that different $K_L$ can be obtained, then $R_L$ at corresponding temperature was calculated according to the formula:

$$R_L = \frac{1}{1 + K_L C_0}; R_L > 1$$

indicates that the adsorption process is disadvantageous (unfavorable); $R_L=1$ indicates that the adsorption isotherm is linear; $0<R_L<1$ indicates that the adsorption process is advantageous (favorable); and $R_L=0$ indicates that the adsorption is an irreversible process. It can be obtained from the experiment that $K_L$ is a positive value, therefore there is $0<R_L<1$, which indicates that the adsorption process is advantageous (favorable). It is illustrated that the adsorption is advantageous with the increase of temperature.

The invention claimed is:

1. A method for separating butanol, comprising the following steps:
   1) adsorbing butanol in a mixed solution by a hydrophobic macroporous polymer adsorbent to reach saturation;
   2) desorbing butanol from the macroporous polymer adsorbent through a method of thermal desorption.

2. The method according to claim 1, wherein the adsorption temperature in the step 1) is 30~37° C.

3. The method according to claim 2, wherein the step 1) comprises the step of shaking the mixed solution at a rate of 20~250 rpm during adsorption.

4. The method according to claim 1, wherein the weight volume ratio (g/mL) of the hydrophobic macroporous polymer adsorbent to the mixed solution used in the step 1) is 1:50.

5. The method according to claim 1, wherein the desorption temperature in the step 2) is above 120° C.

6. The method according to claim 1, wherein the initial concentration of the butanol in the mixed solution is 5350 g/L.

7. The method according to claim 6, wherein the mixed solution further comprises ethanol and acetone.

8. The method according to claim 7, wherein acetone, butanol, and ethanol are from fermentation broth.

9. The method according to claim 8, wherein the butanol is n-butanol.

10. The method according to claim 1, wherein the method further comprising the step of regenerating the hydrophobic macroporous polymer adsorbent.

11. The method according to claim 10, wherein the regeneration of the hydrophobic macroporous polymer adsorbent and desorption of the butanol are completed simultaneously.

12. The method according to claim 1, wherein the hydrophobic macroporous polymer adsorbent is selected from the group consisting of styrene-diethyl benzene, polyacrylamide, amide group cyano group, phenolic hydroxyl, and combinations thereof.

13. The method according to claim 1, wherein the inner surface area of the hydrophobic macroporous polymer adsorbent is 100~2,000 m²/g.

14. The method according to claim 13, wherein the particle size of the hydrophobic macroporous polymer adsorbent is 20~60 mesh.

15. The method according to claim 1, wherein the particle size of the hydrophobic macroporous polymer adsorbent is 20~60 mesh.

16. The method according to claim 1, wherein the pore diameter of the hydrophobic macroporous polymer adsorbent is 11~80 nm.

17. The method according to claim 16, wherein the pore volume of the hydrophobic macroporous polymer adsorbent is 0.4~3 cm³/g.

18. The method according to claim 1, wherein the pore volume of the hydrophobic macroporous polymer adsorbent is 0.4~3 cm³/g.

19. The method according to claim 1, wherein the wet apparent density of the hydrophobic macroporous polymer adsorbent is 590~750 g/L.

20. The method according to claim 19, wherein the water content of the hydrophobic macroporous polymer adsorbent is 40~80%.

21. The method according to claim 1, wherein the water content of the hydrophobic macroporous polymer adsorbent is 40~80%.

* * * * *

UNITED STATES PATENT AND TRADEMARK OFFICE
CERTIFICATE OF CORRECTION

PATENT NO.         : 8,766,019 B2
APPLICATION NO.    : 13/814490
DATED              : July 1, 2014
INVENTOR(S)        : Hanjie Ying et al.

It is certified that error appears in the above-identified patent and that said Letters Patent is hereby corrected as shown below:

In the Claims

Col. 7, line 44, Claim 6         Delete "5350 g/L",

Insert --5~350 g/L--

Col. 8, line 29, Claim 16        Delete "11~80 nm:",

Insert --1~180 nm--

Signed and Sealed this
Seventh Day of June, 2016

Michelle K. Lee
*Director of the United States Patent and Trademark Office*